United States Patent [19]
Gregg et al.

[11] Patent Number: 6,066,653
[45] Date of Patent: May 23, 2000

[54] METHOD OF TREATING ACID LIPASE DEFICIENCY DISEASES WITH AN MTP INHIBITOR AND CHOLESTEROL LOWERING DRUGS

[75] Inventors: Richard E. Gregg, Pennington, N.J.; John R. Wetterau, II, Langhorne, Pa.

[73] Assignee: Bristol-Myers Squibb Co., Princeton, N.J.

[21] Appl. No.: 09/005,437

[22] Filed: Jan. 10, 1998

Related U.S. Application Data

[60] Provisional application No. 60/036,183, Jan. 17, 1997.

[51] Int. Cl.⁷ .......................... A61K 31/445; A61K 31/21
[52] U.S. Cl. .......................... 514/325; 514/510; 514/824
[58] Field of Search .................................... 514/325, 510, 514/824

[56] References Cited

U.S. PATENT DOCUMENTS

| | | | |
|---|---|---|---|
| 4,346,227 | 8/1982 | Terahara et al. | 560/119 |
| 5,712,279 | 1/1998 | Biller et al. | 514/252 |

FOREIGN PATENT DOCUMENTS

| | | |
|---|---|---|
| 643057A1 | 3/1995 | European Pat. Off. . |
| WO96/26205 | 8/1996 | WIPO . |

OTHER PUBLICATIONS

Scriver et al "The Metabolic and Molecular Bases of Inherited Disease", Seventh Edition, vol. II, Chapter 82, "Acid Lipase Deficiency: Wolman Disease and Cholesteryl Ester Storage Disease", pp. 2563–2587, (1995).

Scriver et al "The Metabolic and Molecular Bases of Inherited Disease", Seventh Edition, vol. II, Chapter 85, "Niemann–Pick Disease Type C: A Cellular Cholesterol Lipidosis", pp. 2625–2639, (1995).

*Primary Examiner*—Kimberly Jordan
*Attorney, Agent, or Firm*—Burton Rodney; Ronald S. Hermenau

[57] ABSTRACT

A method is provided for inhibiting or treating diseases associated with acid lipase deficiency by administering to a patient an MTP inhibitor, alone or optionally, in combination with another cholesterol lowering drug, such as pravastatin.

27 Claims, No Drawings

METHOD OF TREATING ACID LIPASE DEFICIENCY DISEASES WITH AN MTP INHIBITOR AND CHOLESTEROL LOWERING DRUGS

This application claims the benefit of U.S. Provisional Application Ser. No. 60/036,183, filed Jan. 17, 1997.

FIELD OF THE INVENTION

The present invention related to a method for inhibiting or treating diseases associated with acid lipase deficiency, including Wolman disease and/or cholesteryl ester storage disease, by administering an MTP inhibitor alone or in combination with another cholesterol lowering drug, such as pravastatin.

BACKGROUND OF THE INVENTION

Wolman disease and cholesteryl ester storage disease are characterized by a deficiency in activity of lysosomal acid lipase which results in massive accumulation of cholesteryl esters and triglycerides in most tissues of the body. Cholesteryl esters and triglycerides are derived from plasma lipoproteins taken up by the cells and are substrates for acid lipase. Acid lipase is responsible for the hydrolysis of cholesteryl esters and triglycerides in the lysosomes.

If plasma cholesterol levels are lowered sufficiently, then cholesteryl ester and triglyceride accumulation in the lysosomes and the consequences of the accumulation could be minimized.

Wolman disease is the more severe of the two diseases and is almost always fatal before the age of 1 year. In contrast, cholesteryl ester storage disease may go undetected until adulthood by which time lipid deposition is widespread. Hyperbetalipoproteinemia is common in cholesteryl ester storage disease, and premature atherosclerosis may be severe.

To date, there has been no specific therapy for acid lipase deficiency other than attempts at suppression of cholesterol synthesis and apolipoprotein B production by 3-hydroxy-3-methylglutaryl coenzyme A reductase inhibitors in combination with cholestyramine treatment and a diet excluding foods rich in cholesterol and triglycerides. The above apparently provided improvement in only one or two cases of cholesteryl ester storage disease. Thus, for the most part, Wolman disease and cholesteryl ester storage disease have been untreatable.

See Scriver, C. R. et al "The Metabolic and Molecular Bases of Inherited Disease", Vol. II (1995), Chap. 82, "Acid Lipase Deficiency: Wolman Disease and Cholesteryl Ester Storage Disease", pp. 2563–2587.

Until now, there have not been any therapeutic agents available which could lower plasma cholesterol levels sufficiently to minimize cholesteryl ester and triglyceride accumulation in the lysosomes.

The microsomal triglyceride transfer protein (MTP) catalyzes the transport of triglyceride (TG), cholesteryl ester (CE), and phosphatidylcholine (PC) between small unilamellar vesicles (SUV). Wetterau & Zilversmit, Chem. Phys. Lipids 38, 205–22 (1985). When transfer rates are expressed as the percent of the donor lipid transferred per time, MTP expresses a distinct preference for neutral lipid transport (TG and CE), relative to phospholipid transport. The microsomal triglyceride transfer protein from bovine liver has been isolated and extensively characterized (1). This has led to the cloning of cDNA expressing the protein from several species, including humans (2). MTP is composed of two subunits. The small subunit is the previously characterized multifunctional protein, protein disulfide isomerase. This is supported by biochemical analysis of the protein (3) as well as co-expression studies performed in insect Sf9 cells using the baculovirus expression system. Expression of soluble active MTP requires the co-expression of PDI and the unique large subunit of MTP (4).

1: Wetterau, J. R. and Zilversmit, D. B. (1985) Chem. Phys. Lipids 38, 205–222.
  Wetterau, J. R., et al, (1990) J. Biol. Chem. 265, 9800–9807.
  Wetterau, J. R., et al, (1991) Biochemistry 30, 4406–4412.
  Atzel, A., and Wetterau, J. R. (1993) Biochemistry 32, 10444–10450.
  Atzel, A., and Wetterau, J. R. (1994) Biochemistry 33, 15382–15388.
  Jamil, H., et al, (1995) J. Biol. Chem. 270, 6549–6554.
2. Sharp, D. et al, (1993) Nature 365, 65–69.
  Lin, M. C. M., et al, J. Biol. Chem. 269, 29138–29145.
  Nakamuta, M., et al, (1996) Genomics 33, 313–316.
3. Wetterau, J. R., et al, (1990) J. Biol. Chem. 265, 9800–9807.
  Wetterau, J. R., et al, (1991) Biochemistry 30, 9728–9735.
4. Ricci, B., et al, (1995) J. Biol. Chem. 270, 14281–14285.

In vitro, MTP catalyzes the transport of lipid molecules between phospholipid membranes. Presumably, it plays a similar role in vivo, and thus plays some role in lipid metabolism. The subcellular (lumen of the microsomal fraction) and tissue distribution (liver and intestine) of MTP have led to speculation that it plays a role in the assembly of plasma lipoproteins, as these are the sites of plasma lipoprotein assembly. Wetterau & Zilversmit, Biochem. Biophys. Acta 875, 610–7 (1986). The ability of MTP to catalyze the transport of TG between membranes is consistent with this hypothesis, and suggests that MTP may catalyze the transport of TG from its site of synthesis in the endoplasmic reticulum (ER) membrane to nascent lipoprotein particles within the lumen of the ER.

Abetalipoproteinemia is an autosomal recessive disease characterized by a virtual absence of plasma lipoproteins which contain apolipoprotein B (apoB). Kane & Havel in The Metabolic Basis of Inherited Disease, Sixth edition, 1139–64 (1989). Plasma TG levels may be as low as a few mg/dL, and they fail to rise after fat ingestion. Plasma cholesterol levels are often only 20–45 mg/dL. These abnormalities are the result of a genetic defect in the assembly and/or secretion of very low density lipoproteins (VLDL) in the liver and chylomicrons in the intestine. The molecular basis for this defect had not been previously determined. In subjects examined, triglyceride, phospholipid, and cholesterol synthesis appear normal. At autopsy, subjects are free of atherosclerosis. Schaefer et al., Clin. Chem. 34, B9–12 (1988). A link between the apoB gene and abetalipoproteinemia has been excluded in several families. Talmud et al., J. Clin. Invest. 82, 1803–6 (1988) and Huang et al., Am. J. Hum. Genet. 46, 1141–8 (1990).

Recent reports (5) demonstrate that the defect causing abetalipoproteinemia is in the MTP gene, and as a result, the MTP protein. When examined, individuals with abetalipoproteinemia have no MTP activity, as a result of mutations in the MTP gene, some of which have been characterized. These results indicate that MTP is required for the synthesis of apoB containing lipoproteins, such as VLDL, the precursor to LDL. It therefore follows that inhibitors of MTP would inhibit the synthesis of VLDL and LDL, thereby lowering VLDL levels, LDL levels, cholesterol levels, and triglyceride levels in animals and man.

5. Wetterau, J. R., et al, (1992) Science 258, 999–1001.
Sharp, D., et al, (1993) Nature 365, 65–69.
Ricci, B., et al, (1995) J. Biol. Chem. 270, 14281–14285.
Shoulders, C. C., et al, (1993) Hum. Mol. Genetics 2, 2109–2116.
Narcisi, T. M. E., et al, (1995) Am. J. Hum. Genet. 57, 1298–1310.
Rehberg, E. F., et al, J. Biol. Chem (in press).

Canadian Patent Application No. 2,091,102 published Mar. 2, 1994 (corresponding to U.S. application Ser. No. 117,362, filed Sep. 3, 1993 (file DC21b)) which is incorporated herein by reference), reports MTP inhibitors which also block apoB containing lipoprotein secretion in a human hepatic cell line (HepG2 cells). This provides further support for the proposal that an MTP inhibitor would lower apoB containing lipoprotein and lipid levels in vivo. This Canadian patent application discloses a method for identifying the MTP inhibitors.

The use of microsomal triglyceride transfer protein (MTP) inhibitors for decreasing serum lipids including cholesterol and triglycerides and their use in treating atherosclerosis, obesity, hyperglycemia, and pancreatitis is disclosed in WO 96/26205, published Aug. 29, 1996, U.S. application Ser. No. 472,067, filed Jun. 6, 1995 (file DC21e), U.S. application Ser. No. 548,811, filed Jan. 11, 1996 (file DC21h), U.S. provisional application Ser. No. 60/017,224, filed May 9, 1996 (file HX79a*), U.S. provisional application Ser. No. 60/017,253, filed May 10, 1996 (file HX82*), U.S. provisional application Ser. No. 60/017,254, May 10, 1996 (file HX84*) and U.S. provisional application Ser. No. 60/028,216, filed Oct. 1, 1996 (file HX86*).

All of the above U.S. applications are incorporated herein by reference.

DESCRIPTION OF THE INVENTION

In accordance with the present invention, a method is provided for inhibiting or treating a disease associated with acid lipase deficiency, including Wolman disease and/or cholesteryl ester storage disease (CESD), in mammalian species, wherein a therapeutically effective amount of a microsomal triglyceride transfer protein (MTP) inhibitor is administered to a patient in need of treatment.

The MTP inhibitor may optionally be administered in combination with another cholesterol lowering drug or delipidating agent.

The MTP inhibitor alone or optionally in combination with another cholesterol lowering drug is administered systemically, such as orally or parenterally or transdermally, to patients in need of treatment.

In accordance with the present invention, the MTP inhibitor lowers plasma cholesterol (LDL-cholesterol) to at least about 50% of normal LDL blood level, preferably down to less than about 25% of normal, and most preferably down to less than about 15% of normal, and lowers triglycerides to at least about 50% of normal triglyceride blood level, and preferably down to about 25% or less of normal, and thereby minimizes cholesteryl ester and triglyceride accumulation in the lysosomes.

The terms "another cholesterol lowering drug or agent" or "another delipidating drug" will be employed interchangeably herein.

MTP inhibitors to be employed in the methods of the invention include MTP inhibitors disclosed in Canadian Patent Application Ser. No. 2,091,102 described hereinbefore (corresponding to U.S. application Ser. No. 117,362), WO 92/26205 published Aug. 29, 1996, U.S. application Ser. No. 472,067, filed Jun. 6, 1995 (file DC21e), U.S. application Ser. No. 548,811, filed Jan. 11, 1996 (file DC21h), U.S. provisional application Ser. No. 60/017,224, filed May 9, 1996 (file HX79a*), U.S. provisional application Ser. No. 60/017,253, filed May 10, 1996 (file HX82*), U.S. provisional application Ser. No. 60/017,254, filed May 10, 1996 (file HX84*), and U.S. provisional application Ser. No. 60/028,216, filed Oct. 1, 1996 (file HX86*). Preferred are each of the preferred MTP inhibitors disclosed in each of the above applications.

All of the above U.S. applications are incorporated herein by reference.

The MTP inhibitors disclosed in U.S. Application Ser. No. 472,067, filed June 6, 1995 (file DC21e) are piperidine compounds of the structure

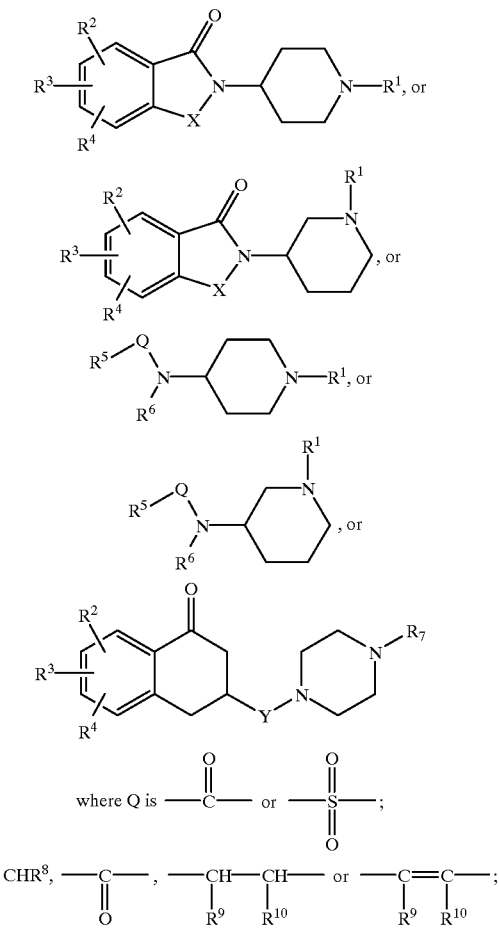

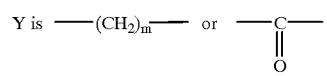

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

Y is —$(CH_2)_m$— or —C(=O)— wherein m is 2 or 3;

$R^1$ is alkyl, alkenyl, alkynyl, aryl, heteroaryl, arylalkyl wherein alkyl has at least 2 carbons, diarylalkyl, arylalkenyl, diarylalkenyl, arylalkynyl, diarylalkynyl, diarylalkylaryl, heteroarylalkyl wherein alkyl has at least 2 carbons, cycloalkyl, or cycloalkylalkyl wherein alkyl has at least 2 carbons, all optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo;

or $R^1$ is a fluorenyl-type group of the structure

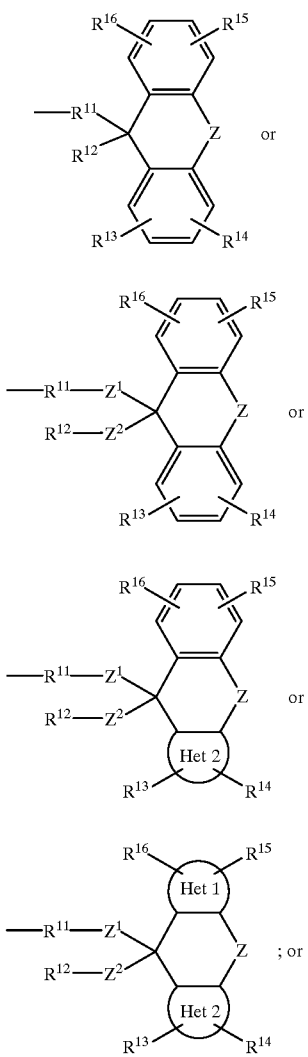

$R^1$ is an indenyl-type group of the structure

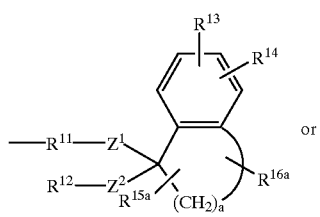

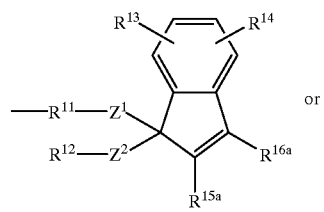

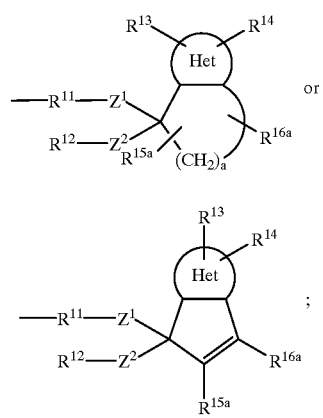

$Z^1$ and $Z^2$ are the same or different and are independently a bond, O, S,

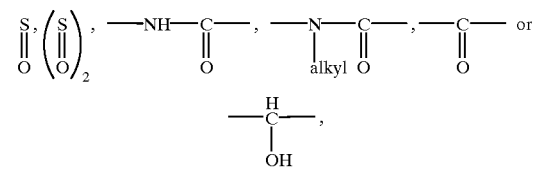

with the proviso that with respect to B, at least one of $Z^1$ and $Z^2$ will be other than a bond; $R^{11}$ is a bond, alkylene, alkenylene or alkynylene of up to 10 carbon atoms; arylene or mixed arylene-alkylene; $R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cycloalkyl, aryloxy, alkoxy, arylalkoxy or cycloalkylalkyl, with the provisos that preferably (1) when $R^{12}$ is H, aryloxy, alkoxy or arylalkoxy, then $Z^2$ is

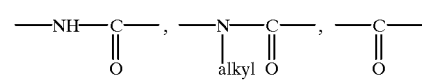

or a bond and (2) when $Z^2$ is a bond, $R^{12}$ cannot be heteroaryl or heteroarylalkyl;

Z is a bond, O, S, N-alkyl, N-aryl, or alkylene or alkenylene from 1 to 5 carbon atoms; $R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl or aryloxy;

$R^{15a}$ and $R^{16a}$ are independently hydrogen, alkyl, halo, haloalkyl, aryl, cycloalkyl, cycloheteroalkyl, alkenyl, alkynyl, alkoxy, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

or $R^1$ is a group of the structure

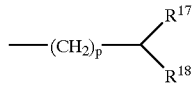

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl at least one of $R^{17}$ and $R^{18}$ being other than H;

or $R^1$ is a group of the structure

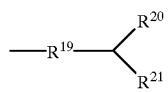

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$ $R^3$ $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is independently alkyl, alkenyl, alkynyl, aryl, alkoxy, aryloxy, arylalkoxy, heteroaryl, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl;

$R^6$ is hydrogen or $C_1$–$C_4$ alkyl or $C_1$–$C_4$ alkenyl; all optionally substituted with 1, 2, 3 or 4 groups which may independently be any of the substituents listed in the definition of $R^5$ set out above;

$R^7$ is alkyl, aryl or arylalkyl wherein alkyl by itself or as part of arylalkyl is optionally substituted with oxo

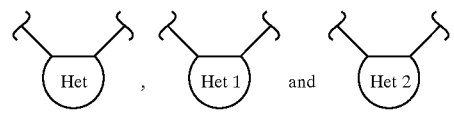

are the same or different and are independently selected from heteroaryl containing 5- or 6-ring members; and N-oxides

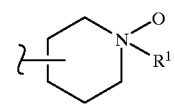

R thereof; and pharmaceutically acceptable salts thereof; with the provisos that preferably where in the first formula X is $CH_2$, and $R^2$, $R^3$ and $R^4$ are each H, then $R^1$ will be other than 3,3-diphenylpropyl, and preferably in the fifth formula, where one of $R^2$, $R^3$ and $R^4$ is 6-fluoro, and the others are H, $R^7$ will be other than 4-(2-methoxyphenyl).

The MTP inhibitors disclosed in U.S. application Ser. No. 548,811 filed Jan. 11, 1996 (file DC21h), have the structure

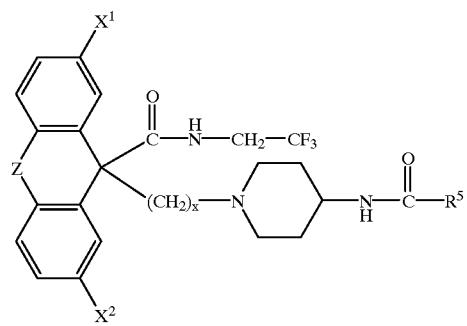

including the piperidine N-oxide thereof or a pharmaceutically acceptable salt thereof, wherein Z is a bond, O or S;

$X^1$ and $X^2$ are independently selected from H or halo;

x is an integer from 2 to 6;

$R^5$ is heteroaryl, aryl, heterocycloalkyl or cycloalkyl, each $R^5$ group being optionally substituted with 1, 2, 3 or 4 substituents which may be the same or different.

The MTP inhibitors disclosed in U.S. provisional application Ser. No. 60/017,224, filed May 9, 1996 (file HX79a*) have the structure

I

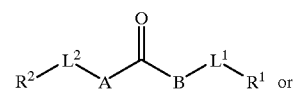

-continued

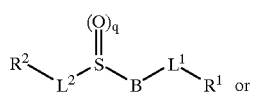
IA

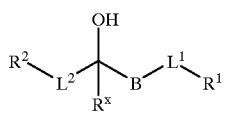
IB including pharmaceutically acceptable salts thereof, wherein q is 0, 1 or 2;

A is (1) a bond;
(2) —O—; or

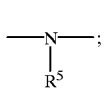
(3)

where $R^5$ is H or lower alkyl or $R^5$ together with $R^2$ forms a carbocyclic or heterocyclic ring system containing 4 to 8 members in the ring.

B is a fluorenyl-type group of the structure:

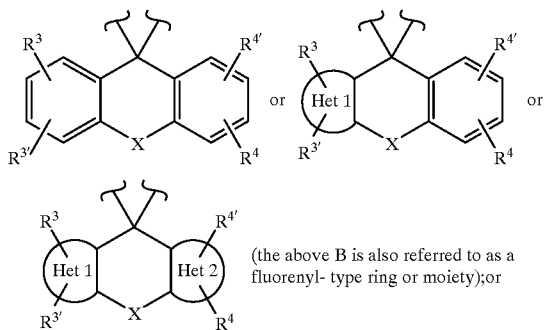

(the above B is also referred to as a fluorenyl- type ring or moiety);or

B is an indenyl-type group of the structure

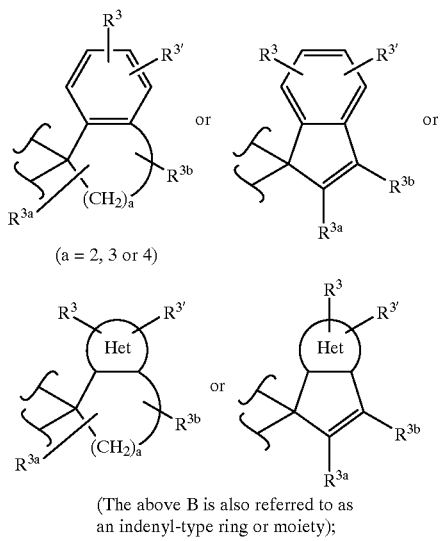

(The above B is also referred to as an indenyl-type ring or moiety);

$R^x$ is H, alkyl or aryl;

$R^1$ is alkyl, alkenyl, alkynyl, alkoxyl, (alkyl or aryl)$_3$Si (where each alkyl or aryl group is independent), cycloalkyl, cycloalkenyl, substituted alkylamino, substituted arylalkylamino, aryl, arylalkyl, arylamino, aryloxy, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, —PO ($R^{13}$) ($R^{14}$), (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); $R^1$ can also be aminocarbonyl (where the amino may optionally be substituted with one or two aryl, alkyl or heteroaryl groups); cyano, 1,1-(alkoxyl or aryloxy)$_2$alkyl (where the two aryl or alkyl substituents can be independently defined, or linked to one another to form a ring, such as 1,3-dioxane or 1,3-dioxolane, connected to $L^1$ (or $L^2$ in the case of $R^2$) at the 2-position); 1,3-dioxane or 1,3-dioxolane connected to $L^1$ (or $L^2$ in the case of $R^2$) at the 4-position.

The $R^1$ group may have from one to four substituents, which can be any of the $R^3$ groups or $R^1$ groups, and any of the preferred $R^1$ substituents set out below.

$R^1$ may be substituted with the following preferred substituents: alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino,

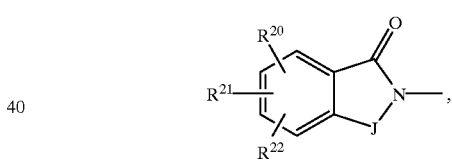

where J is: $CHR^{23}$, —C(=O)—, —CH($R^{24}$)—CH($R^{25}$)—, or
—C($R^{24}$)=C($R^{25}$)—;

$R^{23}$, $R^{24}$ and $R^{25}$ are independently hydrogen, alkyl, alkenyl, alkynyl, aryl, arylalkyl, heteroaryl, heteroarylalkyl, cycloalkyl, or cycloalkylalkyl;

$R^{20}$, $R^{21}$, $R^{22}$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these preferred substituents may either be directly attached to $R^1$, or attached via an alkylene chain at an open position.

$R^2$ is the same or different from $R^1$ and is independently any of the groups set out for $R^1$, H, polyhaloalkyl (such as $CF_3CH_2$, $CF_3CF_2CH_2$ or $CF_3$) or cycloheteroalkyl, and may be substituted with one to four of any of the groups defined for $R^3$, or any of the substituents preferred for $R^1$.

$L^1$ is a linking group containing from 1 to 10 carbons in a linear chain (including alkylene, alkenylene or alkynylene), which may contain, within the linking chain any of the following: one or two alkenes, one or two alkynes, an oxygen, an amino group optionally substituted with alkyl or aryl, an oxo group; and may be substituted with one to five alkyl or halo groups (preferably F).

$L^2$ may be the same or different from $L^1$ and may independently be any of the $L^1$ groups set out above or a singe bond.

$R^3$, $R^{3\prime}$, $R^4$ and $R^{4\prime}$ may be the same or different and are independently selected from H, halogen, $CF_3$, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar, Ar-alkyl, Ar-O, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

$R^{3a}$ and $R^{3b}$ are the same or different and are independently any of the $R^3$ groups except hydroxy, nitro, amino or thio;

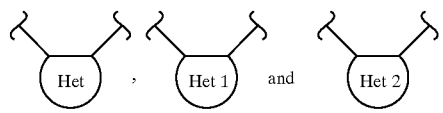

are the same or different and independently represent a 5 or 6 membered heteroaryl ring which may contain 1, 2, 3 or 4 heteroatoms in the ring which are independently N, S or O; and including N-oxides.

X (in the fluorenyl type ring) is a bond, or is one of the following groups:

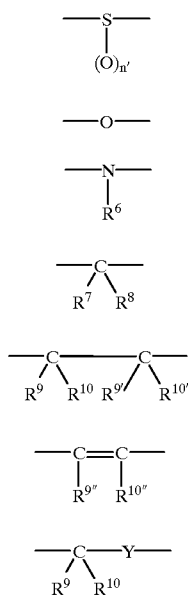

wherein
Y is O, N—$R^6$ or S;
n' is 0, 1 or 2;

$R^6$ is H, lower alkyl, aryl, —C(O)—$R^{11}$ or —C(O)—O—$R^{11}$;

$R^7$ and $R^8$ are the same or different and are independently H, alkyl, aryl, halogen, —O—$R^{12}$, or $R^7$ and $R^8$ together can be oxygen to form a ketone;

$R^9$, $R^{10}$, $R^{9\prime}$ and $R^{10\prime}$ are the same or different and are independently H, lower alkyl, aryl or —O—$R^{11}$;

$R^{9\prime\prime}$ and $R^{10\prime\prime}$ are the same or different and are independently H, lower alkyl, aryl, halogen or —O—$R^{11}$;

$R^{11}$ is alky or aryl;

$R^{12}$ is H, alkyl or aryl.

The following provisos apply to formula I preferred compounds:

(a) when $R^1$ is unsubstituted alkyl or unsubstituted arylalkyl, $L^1$ cannot contain amino;

(b) when $R^1$ is alkyl, $L^1$ cannot contain amino and oxo in adjacent positions (to form an amido group);

(c) when $R^2L^2A$— is $H_2N$—, $R^1L^1$ cannot contain amino;

(d) when $R^1$ is cyano, $L^1$ must have more than 2 carbons;

(e) $R^1L^1$ must contain at least 3 carbons.

With respect to compounds IA and IB, $R^2L^2$ cannot have an O or N atom directly attached to $S=(O)_q$ or $CR^x(OH)$, and for IA, $R^2L^2$ cannot be H.

With respect to preferred compounds of formula IA and IB, where $R^1$ is cycloheteroalkyl, $R^1$ is exclusive of 1-piperidinyl, 1-pyrrolidinyl, 1-azetidinyl or 1-(2-oxopyrrolidinyl).

The MTP inhibitors disclosed in U.S. provisional application Ser. No. 60/017,253, filed May 10, 1996, (file HX82*) are pyrrolidine compounds and have the structure

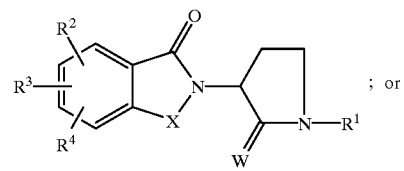

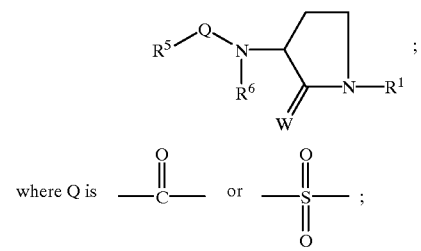

W is H,H or O;

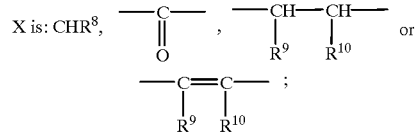

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

R¹ is alkyl, alkenyl, alkynyl, aryl, heteroaryl, arylalkyl (wherein alkyl preferably has at least 2 carbons, more preferably at least 3 carbons), diarylalkyl, arylalkenyl, diarylalkenyl, arylalkynyl, diarylalkynyl, diarylalkylaryl, heteroarylalkyl (wherein alkyl preferably has at least 2 carbons, more preferably at least 3 carbons), cycloalkyl, or cycloalkylalkyl (wherein alkyl preferably has at least 2 carbons, more preferably at least 3 carbons); all of the aforementioned R¹ groups being optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo; or R¹ is a fluorenyl-type group of the structure

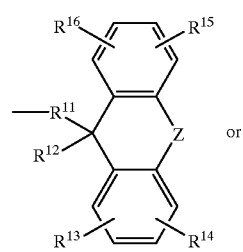

A

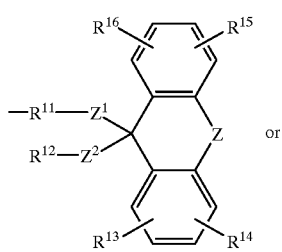

B

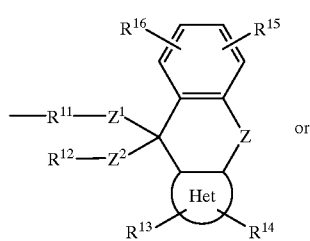

C

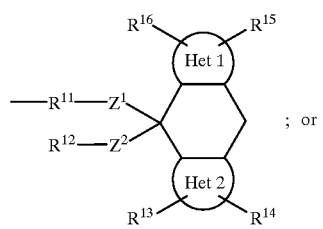

D

R¹ is an indenyl-type group of the structure

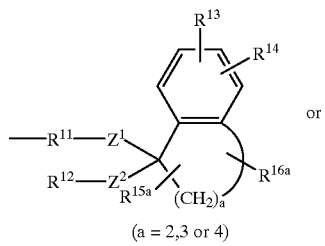

E

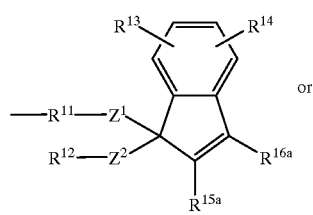

F

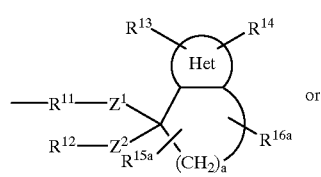

G

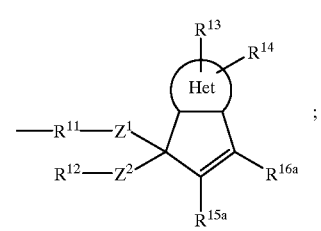

H $Z^1$ and $Z^2$ are the same or different and are independently a bond, O, S,

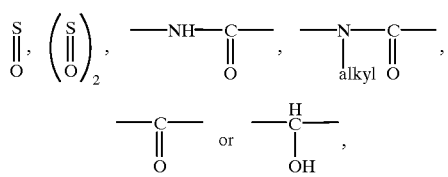

with the proviso that with respect to B, at least one of $Z^1$ and $Z^2$ will be other than a bond;

$R^{11}$ is a bond, alkylene, alkenylene or alkynylene of up to 10 carbon atoms, arylene (for example

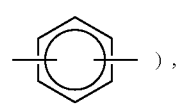), or mixed arylene-alkylene (for example

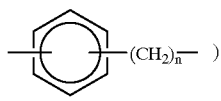

where n is 1 to 6;

$R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cycloalkyl, aryloxy, alkoxy, arylalkoxy or cycloalkylalkyl; with the provisos that (1) when $R^{12}$ is H, aryloxy, alkoxy or arylalkoxy, then $Z^2$ is

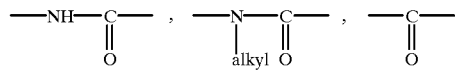

or a bond;

and (2) when $Z^2$ is a bond, $R^{12}$ cannot be heteroaryl or heteroarylalkyl;

Z is a bond, O, S, N-alkyl, N-aryl, or alkylene or alkenylene of from 1 to 5 carbon atoms;

$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

$R^{15a}$ and $R^{16a}$ are independently any of the $R^{15}$ or $R^{16}$ groups except hydroxy, nitro, amino or thio;

or $R^1$ is

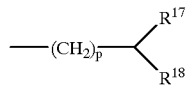

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;

or $R^1$ is

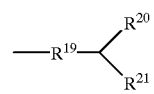

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is alkyl, alkenyl, alkynyl, aryl, alkoxy, aryloxy, arylalkoxy, heteroaryl, arylalkyl, heteroarylalkyl, cycloalkyl, cycloheteroalkyl, heteroaryloxy, cycloalkylalkyl, polycycloalkyl, polycycloalkylalkyl, cycloalkenyl, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all of the $R^5$ substituents and $R^6$ substituents (set out hereinafter) being optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, aryl or heteroaryl, or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl. Where $R^5$ is phenyl, aryl, heteroaryl or cycloalkyl; this group preferably includes an ortho hydrophobic substituent such as alkyl, haloalkyl (with up to 5 halo groups), alkoxy, haloalkoxy (with up to 5 halo groups), aryl, aryloxy or arylalkyl;

$R^6$ is hydrogen or $C_1$—$C_4$ alkyl or $C_1$—$C_4$ alkenyl;

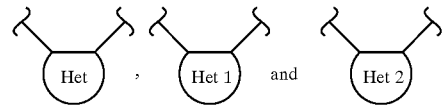

are the same or different and are independently selected from heteroaryl containing 5- or 6-ring members; and including N-oxides of the formulae I and II compounds, that is

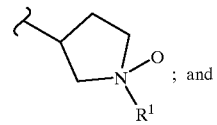

including pharmaceutically acceptable salts thereof.

The MTP inhibitors disclosed in U.S. provisional application Ser. No. 60/017,254, filed May 10, 1996, (file HX84*) are azetidine compounds which have the structure

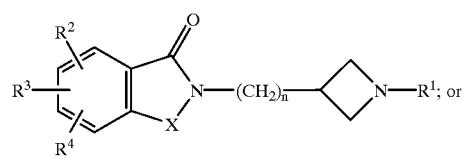

I

-continued

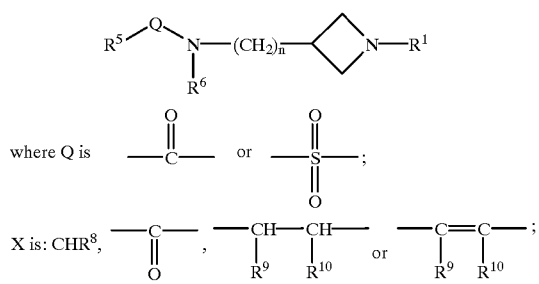
II where Q is ─C─ or ─S─ ;
         ‖        ‖
         O        O

X is: CHR$^8$, ─C─, ─CH─CH─ or ─C═C─ ;
              ‖    |   |       |   |
              O    R$^9$ R$^{10}$   R$^9$ R$^{10}$

R$^8$, R$^9$ and R$^{10}$ are independently hydrogen, alkyl, alkenyl, alkynyl, aryl, arylalkyl, heteroaryl, heteroarylalkyl, cycloalkyl, or cycloalkylalkyl;

R$^1$ is alkyl, alkenyl, alkynyl, aryl, heteroaryl, arylalkyl (wherein alkyl preferably has at least 2 carbons, more preferably at least 3 carbons), diarylalkyl, arylalkenyl, diarylalkenyl, arylalkynyl, diarylalkynyl, diarylalkylaryl, heteroarylalkyl (wherein alkyl preferably has at least 2 carbons, more preferably at least 3 carbons), cycloalkyl, or cycloalkylalkyl (wherein alkyl preferably has at least 2 carbons, more preferably at least 3 carbons); all of the aforementioned R$^1$ groups being optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo; or R$^1$ is a fluorenyl-type group of the structure

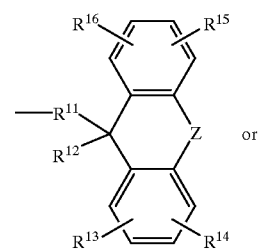
A

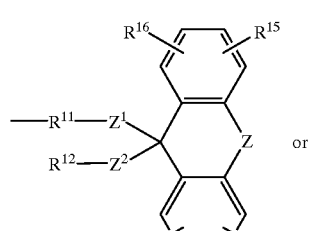
B

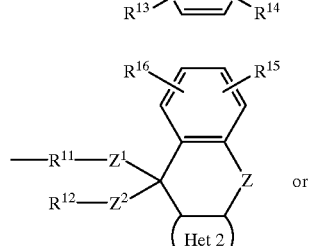
C

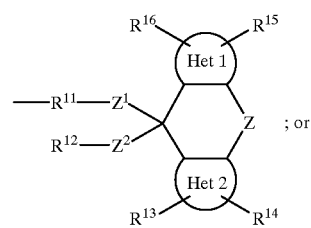
D

R$^1$ is an indenyl-type group of the structure

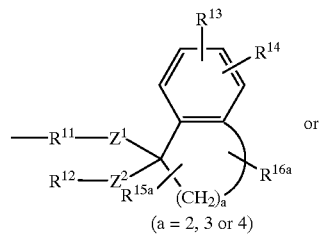
E

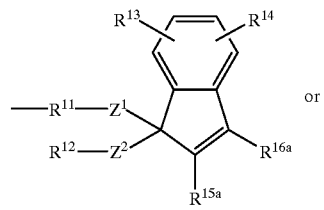
F

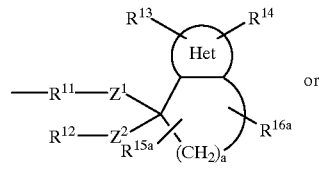
G

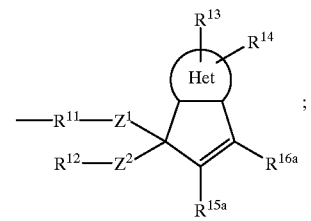
H

Z$^1$ and Z$^2$ are the same or different and are independently a bond, O, S, $$\underset{O}{\overset{S}{\|}}, \left(\underset{O}{\overset{S}{\|}}\right)_2, -NH-\underset{O}{\overset{\|}{C}}-, -\underset{alkyl}{N}-\underset{O}{\overset{\|}{C}}-, -\underset{O}{\overset{\|}{C}}-\ \text{or}$$

$$-\underset{OH}{\overset{H}{\underset{|}{C}}}-,$$

with the proviso that with respect to B, at least one of Z$^1$ and Z$^2$ will be other than a bond;

R$^{11}$ is a bond, alkylene, alkenylene or alkynylene of up to 10 carbon atoms, arylene (for example

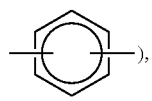

or mixed arylene-alkylene (for example

where q is 1 to 6;

R$^{12}$ is hydrogen, alkyl, alkenyl, aryl, haloalkyl, trihaloalkyl, trihaloalkylalkyl, heteroaryl, heteroarylalkyl, arylalkyl, arylalkenyl, cycloalkyl, aryloxy, alkoxy, arylalkoxy or cycloalkylalkyl; with the provisos that (1) when R$^{12}$ is H, aryloxy, alkoxy or arylalkoxy, then Z$^2$ is

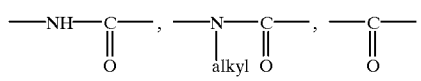

or a bond;

and (2) when Z$^2$ is a bond, R$^{12}$ cannot be heteroaryl or heteroarylalkyl;

Z is a bond, O, S, N-alkyl, N-aryl, or alkylene or alkenylene of from 1 to 5 carbon atoms;

R$^{13}$, R$^{14}$, R$^{15}$, and R$^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

R$^{15a}$ and R$^{16a}$ are independently any of the R$^{15}$ or R$^{16}$ groups except hydroxy, nitro, amino or thio;

or R$^1$ is

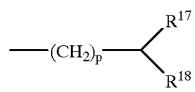

wherein p is 1 to 8 and R$^{17}$ and R$^{18}$ are each independently H, alkyl, alkenyl, aryl, arylalkyl, heteroaryl, heteroarylalkyl, cycloalkyl or cycloalkylalkyl, at least one of R$^{17}$ and R$^{18}$ being other than H;

or R$^1$ is

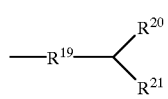

wherein R$^{19}$ is aryl or heteroaryl;

R$^{20}$ is aryl or heteroaryl;

R$^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

R$^2$, R$^3$, R$^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

R$^5$ is alkyl, alkenyl, alkynyl, aryl, alkoxy, aryloxy, arylalkoxy, heteroaryl, arylalkyl, heteroarylalkyl, cycloalkyl, cycloheteroalkyl, heteroaryloxy, cycloalkylalkyl, polycycloalkyl, polycycloalkylalkyl, cycloalkenyl, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all of the R$^5$ substituents and R$^6$ substituents (set out hereinafter) being optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, aryl or heteroaryl, or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl. Where R$^5$ is phenyl, aryl, heteroaryl or cycloalkyl; this group preferably includes an ortho hydrophobic substituent such as alkyl, haloalkyl (with up to 5 halo groups), alkoxy, haloalkoxy (with up to 5 halo groups), aryl, aryloxy or arylalkyl;

R$^6$ is hydrogen or $C_1$–$C_4$ alkyl or $C_1$–$C_4$ alkenyl;

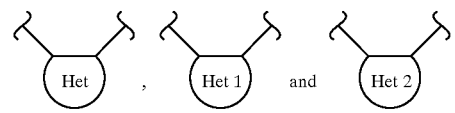

are the same or different and are independently selected from heteroaryl containing 5- or 6-ring members; and including N-oxides of the formulae I and II compounds, that is

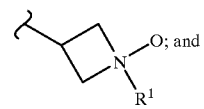

including pharmaceutically acceptable salts thereof.

The MTP inhibitors disclosed in U.S. provisional application Ser. No. 60/028,216, filed Oct. 1, 1996, have the structure

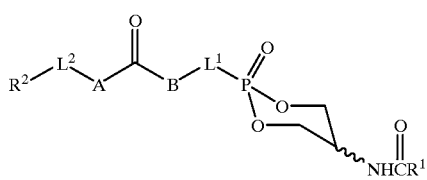

including pharmaceutically acceptable salts thereof, wherein
A is (1) a bond;
(2) —O—; or

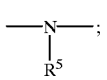   (3)

where $R^5$ is H or lower alkyl or $R^5$ together with $R^2$ forms a carbocyclic or heterocyclic ring system containing 4 to 8 members in the ring.

B is a fluorenyl-type group of the structure:

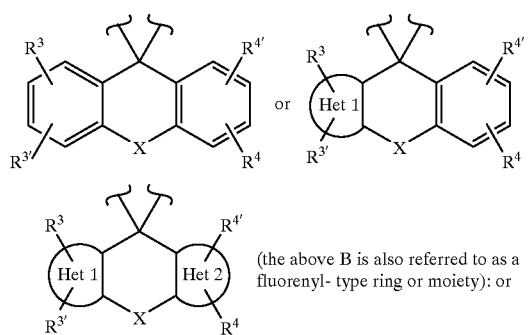

(the above B is also referred to as a fluorenyl- type ring or moiety): or

B is an indenyl-type group of the structure

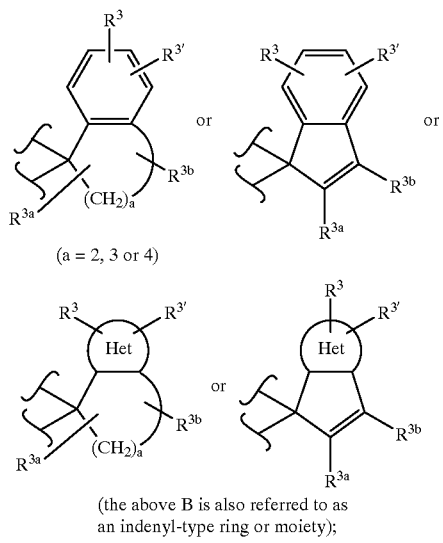

(the above B is also referred to as an indenyl-type ring or moiety);

$R^1$ is independently alkyl, alkenyl, alkynyl, aryl, alkoxy, aryloxy, arylalkoxy, heteroaryl, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl;

$R^2$ is alkyl, alkenyl, alkynyl, alkoxyl, (alkyl or aryl)$_3$Si (where each alkyl or aryl group is independent), cycloalkyl, cycloalkenyl, substituted alkylamino, substituted arylalkylamino, aryl, arylalkyl, arylamino, aryloxy, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, —PO($R^{13}$) ($R^{14}$), (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); $R^1$ can also be aminocarbonyl (where the amino may optionally be substituted with one or two aryl, alkyl or heteroaryl groups); cyano, 1,1-(alkoxyl or aryloxy)$_2$alkyl (where the two aryl or alkyl substituents can be independently defined, or linked to one another to form a ring, such as 1,3-dioxane or 1,3-dioxolane, connected to $L^1$ (or $L^2$ in the case of $R^2$) at the 2-position); 1,3-dioxane or 1,3-dioxolane connected to $L^1$ (or $L^2$ in the case of $R^2$) at the 4-position.

The $R^2$ group may have from one to four substituents, which can be any of the $R^3$ groups or $R^2$ groups, and any of the preferred $R^2$ substituents set out below.

$R^2$ may be substituted with the following preferred substituents: alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino,

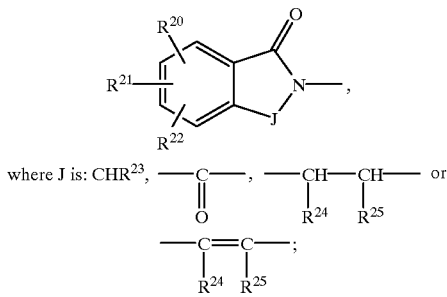

where J is: CHR$^{23}$, —C(=O)—, —CH(R$^{24}$)—CH(R$^{25}$)— or
—C(R$^{24}$)=C(R$^{25}$)—;

R$^{23}$, R$^{24}$ and R$^{25}$ are independently hydrogen, alkyl, alkenyl, alkynyl, aryl, arylalkyl, heteroaryl, heteroarylalkyl, cycloalkyl, or cycloalkylalkyl;

R$^{20}$, R$^{21}$, R$^{22}$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these preferred substituents may either be directly attached to R$^1$, or attached via an alkylene chain at an open position.

L$^1$ is a linking group containing from 1 to 10 carbons in a linear chain (including alkylene, alkenylene or alkynylene), which may contain, within the linking chain any of the following: one or two alkenes, one or two alkynes, an oxygen, an amino group optionally substituted with alkyl or aryl, an oxo group; and may be substituted with one to five alkyl or halo groups (preferably F).

L$^2$ may be the same or different from L$^1$ and may independently be any of the L$^1$ groups set out above or a singe bond.

R$^3$, R$^{3\prime}$, R$^4$ and R$^{4\prime}$ may be the same or different and are independently selected from H, halogen, CF$_3$, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

R$^{3a}$ and R$^{3b}$ are the same or different and are independently any of the R$^3$ groups except hydroxy, nitro, amino or thio;

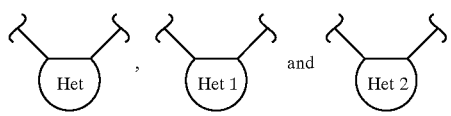

are the same or different and independently represent a 5 or 6 membered heteroaryl ring which may contain 1, 2, 3 or 4 heteroatoms in the ring which are independently N, S or O; and including N-oxides.

X (in the fluorenyl type ring) is a bond, or is one of the following groups:

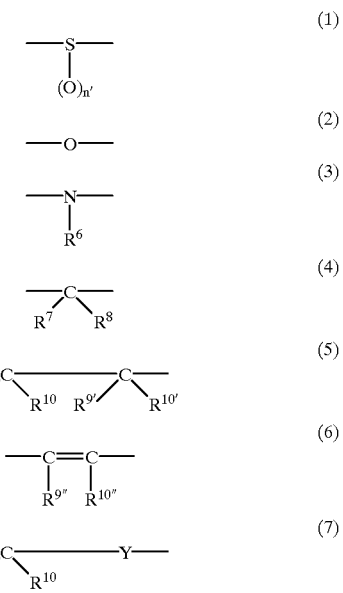

wherein

Y is O, N—R$^6$ or S;

n' is 0, 1 or 2;

R$^6$ is H, lower alkyl, aryl, —C(O)—R$^{11}$ or —C(O)—O—R$^{11}$;

R$^7$ and R$^8$ are the same or different and are independently H, alkyl, aryl, halogen, —O—R$^{12}$, or R$^7$ and R$^8$ together can be oxygen to form a ketone;

R$^9$, R$^{10}$, R$^{9\prime}$ and R$^{10\prime}$ are the same or different and are independently H, lower alkyl, aryl or —O—R$^{11}$;

R$^{9\prime\prime}$ and R$^{10\prime\prime}$ are the same or different and are independently H, lower alkyl, aryl, halogen or —O—R$^{11}$;

R$^{11}$ is alky or aryl;

R$^{12}$ is H, alkyl or aryl.

Compounds disclosed as preferred in each of the above applications are preferred for use in the present invention.

Most preferred MTP inhibitors to be employed in accordance with the present invention include preferred MTP inhibitors as set out in U.S. patent application Ser. No. 548,811, filed Jan. 11, 1996 (file DC21h) and in U.S. provisional application Ser. No. 60/017,224, filed May 9, 1996 (file HX79a*).

Thus, preferred compounds in U.S. patent application Ser. No. 548,811 (file DC21h) for use herein are compounds where Z is a bond;

X$^1$ and X$^2$ are H;

R$^5$ is aryl such as phenyl substituted with (1) aryl such as phenyl,

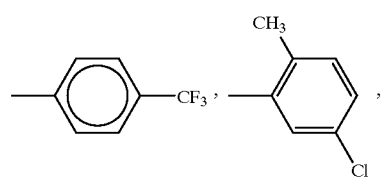

(2) heteroaryl such as

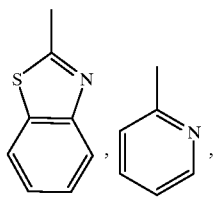

(3) halo such as Cl $R^5$ is heteroaryl such as

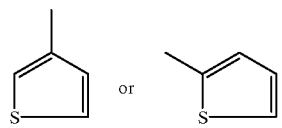

substituted with (1) aroyl such as

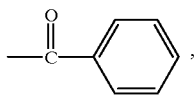

(2) arylthio such as

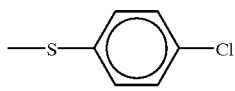

wherein the $R^5$ substituent is preferably in the position adjacent to the carbon linked to

$(CH_2)_x$ is $-(CH_2)_4-$ or

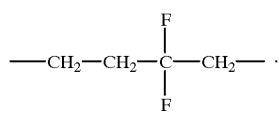

Most preferred is

9-[4-[4-[[2-(2,2,2-trifluoromethyl)-benzoyl]amino]-1-piperidinyl]butyl]-N-(2,2,2-trifluoroethyl)-9H-fluorene-9-carboxamide

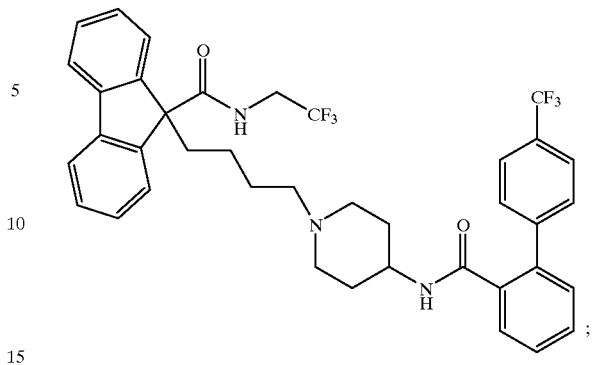

Preferred compounds in U.S. provisional application Ser. No. 60/017,224 (file HX79a*) for use herein are MTP inhibitor compounds of formula I that is

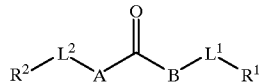

wherein A is NH,

B is

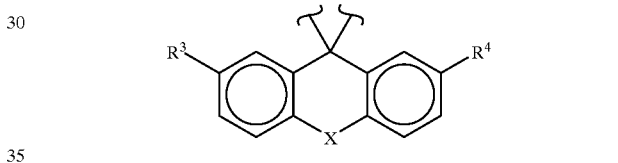

X is a bond, oxygen or sulfur; $R^3$ and $R^4$ are independently H or F.

Preferred $R^1$ groups are aryl, preferably phenyl, heteroaryl, preferably imidazoyl or pyridyl (preferably substituted with one of the preferred $R^1$ substituents: arylcarbonylamino, heteroarylcarbonylamino, cycloalkylcarbonylamino, alkoxycarbonylamino, alkylsulfonylamino, arylsulfonylamino, heteroarylsulfonylamino), PO(OAlkyl)$_2$, heteroarylthio, benzthiazole-2-thio, imidazole-2-thio, alkyl, or alkenyl, cycloalkyl such as cyclohexyl, or 1,3-dioxan-2-yl.

Preferred $R^2$ groups are alkyl, polyfluoroalkyl (such as 1,1,1-trifluoroethyl), alkenyl, aryl or heteroaryl (preferably substituted with one of the preferred $R^1$ substituents above), or PO(OAlkyl)$_2$.

If $R^2$ is alkyl, 1,1,1-trifluoroethyl, or alkenyl, it is preferred that $R^1$ is other than alkyl or alkenyl.

It is preferred that $L^1$ contains 1 to 5 atoms in the linear chain and $L^2$ is a bond or lower alkylene.

Preferred embodiments of formula IA and formula IB compounds of the invention include those where B, $L^1$, $L^2$, $R^1$ and $R^2$ are as set out with respect to the preferred embodiments of the formula I compounds, q is 0 or 2 and $R^x$ is H.

The other cholesterol lowering drugs or delipidating drugs which may be used in the method of the invention include HMG CoA reductase inhibitors, squalene synthetase inhibitors, fibric acid derivatives, bile acid sequestrants, probucol, niacin, niacin derivatives and the like.

The HMG CoA reductase inhibitors suitable for use herein include, but are not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171, with pravastatin, lovastatin or simvastatin being preferred. Other HMG CoA reductase inhibitors which may be employed herein include, but are not limited to, fluvastatin, cerivastatin, atorvastatin, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)alkyl]pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-di-substituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, as well as other known HMG CoA reductase inhibitors.

In addition, phosphinic acid compounds useful in inhibiting HMG CoA reductase suitable for use herein are disclosed in GB 2205837.

The squalene synthetase inhibitors suitable for use herein include, but are not limited to, α-phosphonosulfonates disclosed in U.S. application Ser. No. 08/266,888, filed Jul. 5, 1994 (HX59b), those disclosed by Biller et al, J. Med. Chem. 1988, Vol. 31, No. 10, pp 1869–1871, including isoprenoid (phosphinylmethyl)phosphonates such as those of the formula

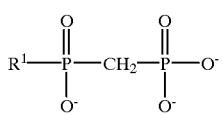

I

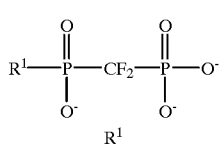

II $R^1$

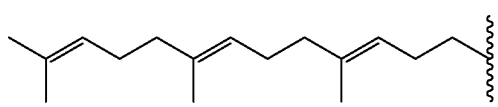

a

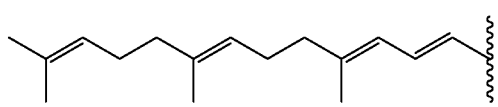

b

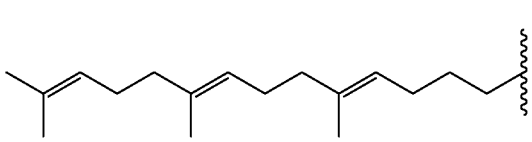

c

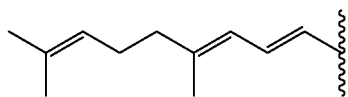

d including the triacids thereof, triesters thereof and tripotassium and trisodium salts thereof as well as other squalene synthetase inhibitors disclosed in U.S. Pat. Nos. 4,871,721 and 4,924,024 and in Biller et al, J. Med. Chem., 1988, Vol. 31, No. 10, pp 1869 to 1871.

In addition, other squalene synthetase inhibitors suitable for use herein include the terpenoid pyrophosphates disclosed by P. Ortiz de Montellano et al, J. Med. Chem.; 1977, 20, 243–249, the farnesyl diphosphate analog A and presqualene pyrophosphate (PSQ-PP) analogs as disclosed by Corey and Volante, J. Am. Chem. Soc. 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U. of Utah, Abstract, Table of Contents, pp. 16, 17, 40–43, 48–51, Summary.

Preferred are pravastatin, lovastatin or simvastatin.

All of the above U.S. applications are incorporated herein by reference.

Other cholesterol lowering drugs suitable for use herein include, but are not limited to, antihyperlipoproteinemic agents such as fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Polidexide®), as well as clofibrate, lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The above-mentioned U.S. patents are incorporated herein by reference.

The MTP inhibitor will be employed in a weight ratio to the other cholesterol lowering or delipidating agent (where present), in accordance with the present invention, within the range from about 500:1 to about 1:500, preferably from about 100:1 to about 1:100.

In carrying out the method of the present invention, the MTP inhibitor alone or optionally in combination with the other cholesterol lowering drug may be administered to mammalian species, such as monkeys, dogs, cats, rats, humans, etc., and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

The dose administered must be carefully adjusted according to age, weight and condition of the patient, as well as the route of administration, dosage form and regimen and the desired result.

The dosages and formulations for the MTP inhibitor will be as disclosed in the various patents and applications discussed above.

The dosages and formulations for the other delipidating agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 100 mg/kg and preferably from about 0.1 mg/kg to about 75 mg/kg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For parenteral administration, the MTP inhibitor will be employed in an amount within the range of from about 0.005 mg/kg to about 10 mg/kg and preferably from about 0.005 mg/kg to about 8 mg/kg, one to four times daily.

The other cholesterol lowering or delipidating agent will be employed in amounts set out in the latest edition of the Physician's Desk Reference (PDR).

For oral administration, a satisfactory result may be obtained employing an HMG CoA reductase inhibitor in dosages employed, for example, pravastatin, lovastatin, simvastatin, atorvastatin, fluvastatin or cerivastatin as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount of from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The serum cholesterol lowering drugs when present will be employed in dosages normally employed as indicated in the Physician's Desk Reference, for each of such agents such as in an amount within the range of from about 2 mg to about 7500 mg and preferably from about 2 mg to about 4000 mg.

A preferred oral dosage form, such as tablets or capsules, will contain MTP inhibitor in an amount of from about 10 to about 400 mg, and the HMG CoA reductase inhibitor (where present) in an amount of from about 0.1 to about 100 mg, preferably from about 5 to about 80 mg, and more preferably from about 10 to about 50 mg.

The MTP inhibitor and other cholesterol lowering drug may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

Tablets of various sizes can be prepared, e.g., of about 2 to 2000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of MTP inhibitor and other cholesterol lowering drug are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the carrier, glycerol as solubilizer, sucrose as sweetening agent, methyl and propyl parabens as preservatives, a dye and a flavoring such as cherry or orange.

Some of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the acid lipase deficiency exists. Sustained release forms of such formulations which may provide such amounts biweekly, weekly, monthly and the like may also be employed.

The following Examples represent preferred embodiments of the present invention.

EXAMPLES 1 AND 2

Formulations suitable for oral administration are prepared as described below.

Capsules containing 1 mg MTP inhibitor BMS 201,038 (Example 1) and capsules containing 50 mg BMS 201,038 (Example 2) are produced from the following ingredients.

| Ingredient | Example 1 Amount (mg/ Capsule) | Example 2 Amount (mg/ Capsule) |
|---|---|---|
| BMS-201038 (1) | 1.1 | 56.9 |
| Lactose, Hydrous, NF | ca. 30.2 | ca. 99.9 |
| Lactose, Anhydrous, NF | 47.3 | 0.0 |
| Microcrystalline Cellulose, NF | 10.0 | 50.0 |
| Pregelatinized Starch, NF | 5.0 | 25.0 |
| Sodium Starch Glycolate, NF | 5.0 | 12.5 |
| Colloidal Silicon Dioxide, NF | 1.0 | 5.0 |
| Magnesium Stearate, NF | 0.3 | 0.6 |
| Purified Water, USP or | q.s. | q.s. |
| Water for Injection, USP | q.s. | q.s. |
| Gray, Opaque, Size #0 Capsule Shell | One Capsule | One Capsule |
| Total Fill Weight | about 100.0 | about 250.0 |

(1) In Example 1 this amount is expressed in terms of the amount of methane sulfonic acid salt per capsule at 100% potency. In Example 2, this amount is expressed in terms of the free base This is equivalent to 1 mg and 50 mg (Examples 1 and 2, respectively) of the free base.

The MTP inhibitor BMS 201,038, and colloidal silicon dioxide are blended in a suitable blender with lactose hydrous, microcrystalline cellulose, pregelatinized starch and a portion of sodium starch glycolate. The resulting blend is wet granulated with water. The wet granulation is dried in a suitable dryer. The remaining portion of sodium starch glycolate is added to the granulation and mixed therein. Magnesium stearate is added to the granulation and mixed therein. The resulting blend is filled into capsules.

EXAMPLE 3

Pravastatin tablets (10, 20 or 40 mg as described in the 1996 PDR) and MTP inhibitor (BMS 201,238) tablets may be administered as a combination in accordance with the teachings of the present invention. In addition, the pravastatin and MTP inhibitor tablets may be ground up into powders and used together in a single capsule.

EXAMPLE 4

Tablets containing 500 mg clofibrate by itself or in combination with 10 mg BMS 201,038 may be employed in separate dosage forms or combined in a single capsule form.

EXAMPLES 5, 6 AND 7

Ciprofibrate, bezafibrate, gemfibrozil alone or in combination with an MTP inhibitor may also be prepared in a manner described hereinbefore in Examples 1 to 3.

What is claimed is:

1. A method for inhibiting or treating a disease associated with acid lipase deficiency in a mammalian species, which comprises administering to a patient in need thereof a therapeutically effective amount of at least one MTP inhibitor to lower plasma cholesterol and triglycerides and thereby minimize cholesteryl ester and triglyceride accumulation in lysosomes.

2. The method as defined in claim 1 wherein the MTP inhibitor is employed in combination with another type of cholesterol lowering drug.

3. The method as defined in claim 2 wherein the other cholesterol lowering drug is an HMG CoA reductase inhibitor, a squalene synthetase inhibitor, a fibric acid derivative, probucol, a bile acid sequestrant, nicotinic acid or neomycin.

4. The method as defined in claim 3 wherein the HMG CoA reductase inhibitor is pravastatin, lovastatin, simvastatin, atorvastatin, fluvastatin or cerivastatin.

5. The method as defined in claim 2 wherein the cholesterol lowering drug is a fibric acid derivative which is gemfibrozil, fenofibrate, clofibrate, bezafibrate, ciprofibrate, clinofibrate, probucol, gemfibrozil, dextrothyroxine or its sodium salt, colestipol or its hydrochloride, cholestyramine, nicotinic acid, neomycin, p-aminosalicylic acid or aspirin.

6. The method as defined in claim 2 wherein the MTP inhibitor is present in a weight ratio to other cholesterol lowering drug within the range from about 500:1 to about 1:500.

7. The method as defined in claim 1 or 2 wherein the MTP inhibitor has the structure

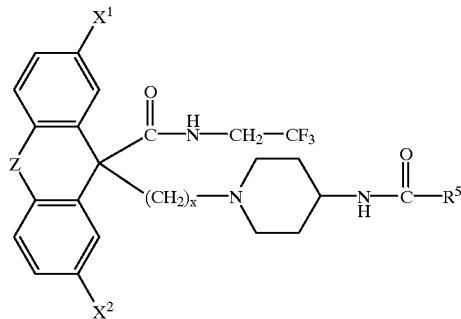

wherein Z is a bond, O or S;

$X^1$ and $X^2$ are independently selected from H or halo;

x is an integer from 2 to 6;

$R^5$ is heteroaryl, aryl, heterocycloalkly or cycloalkyl, each $R^5$ group being optionally substituted with 1, 2, 3 or 4 substituents which may be the same or different;

the piperidine N-oxide thereof, and pharmaceutically acceptable salts thereof.

8. The method as defined in claim 7 where in the MTP inhibitor Z is a bond.

9. The method as defined in claim 7 where the MTP inhibitor is a piperidine N-oxide.

10. The method as defined in claim 7 where in the MTP inhibitor $(CH_2)_x$ is optionally substituted with 1, 2 or 3 substituents which are the same or different and are alkyl or halo.

11. The method as defined in claim 7 where in the MTP inhibitor $R^5$ is substituted with 1, 2, 3 or 4 substituents which may be the same or different and are halogen, monocyclic heteroaryl, bicyclic heteroaryl, heteroarylalkyl, cycloheteroalkyl, alkyl, alkoxy, cycloalkyl, aryl, aryloxy, substituted aryl, arylalkyloxy, heteroaryloxy, amino, alkylamino, alkyl(aryl)amino, heteroarylamino, arylamino, alkylthio, arylthio, arylthioalkyl, heteroarylthio, arylsulfinyl or acyl.

12. The method as defined in claim 7 wherein at least one of the substituents of the MTP inhibitor $R^5$ is attached to a carbon in the position adjacent to the carbon linked to

13. The method as defined in claim 11 where in the MTP inhibitor $R^5$ is substituted with 1, 2, 3 or 4 of one or more of the following I, Cl, F, CF$_3$

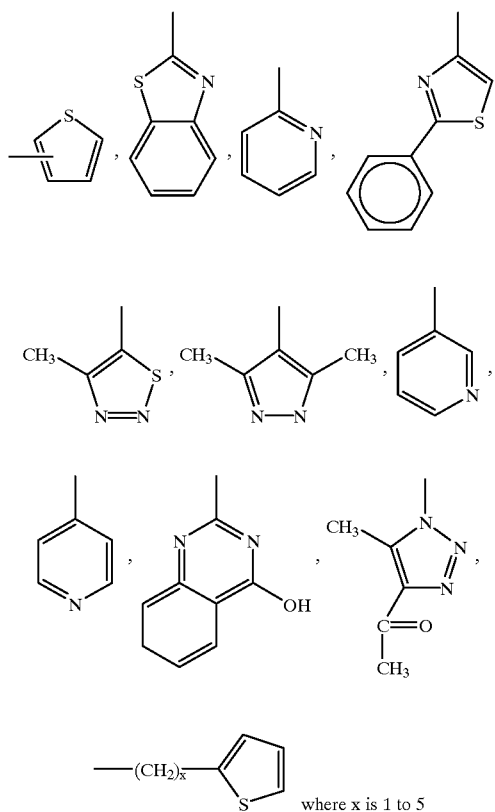

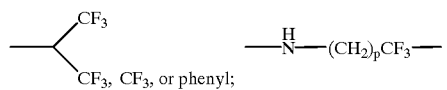
where x is 1 to 5

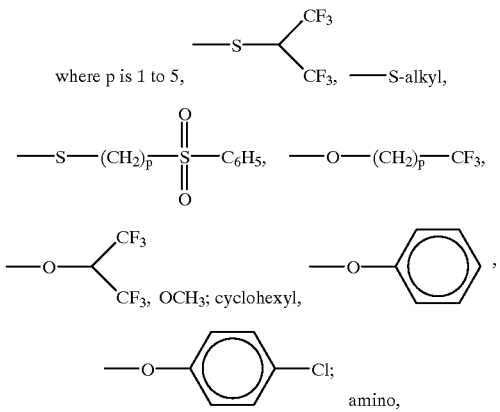

alkyl, phenyl, phenyl substituted with halo, alkyl, CF$_3$O, alkoxy, amino,

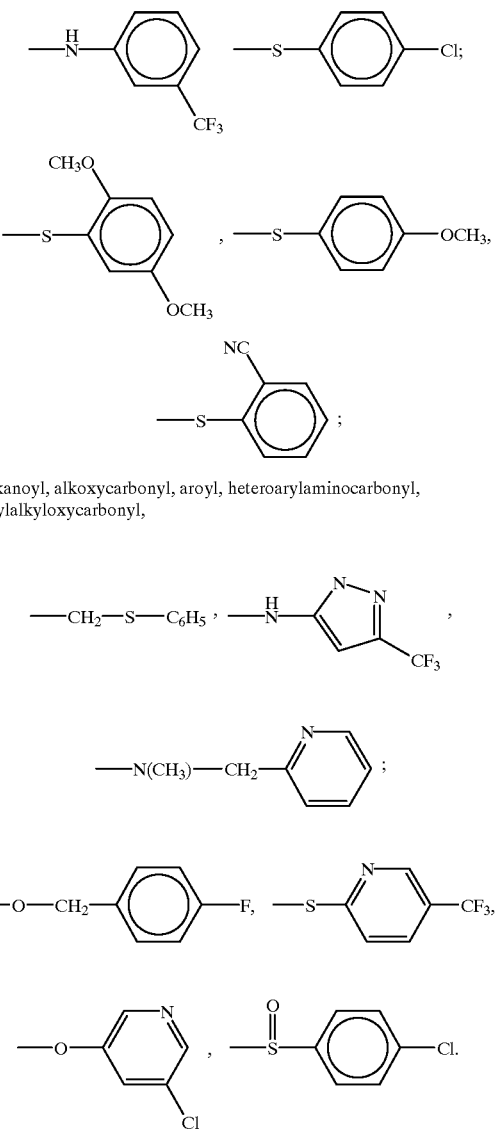

alkanoyl, alkoxycarbonyl, aroyl, heteroarylaminocarbonyl, arylalkyloxycarbonyl,

14. The method as defined in claim 13 where in the MTP inhibitor R$^5$ is phenyl substituted with haloalkylphenyl or heteroaryl.

15. The method as defined in claim 14 where in the MTP inhibitor R$^5$ is

16. The method as defined in claim 13 where in the MTP inhibitor is

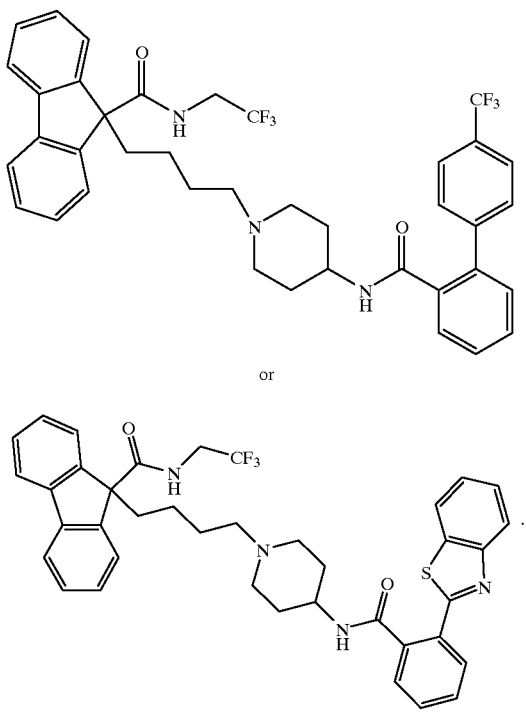

or

17. The method as defined in claim 1 wherein the disease to be treated is Wolman disease.

18. The method as defined in claim 1 wherein the disease to be treated is cholesteryl ester storage disease.

19. The method as defined in claim 1 wherein the MTP inhibitor lowers plasma LDL-cholesterol to at least 50% of normal LDL blood levels, and lowers triglycerides to at least 50% of normal triglyceride blood levels.

20. The method as defined in claim 2 wherein the MTP inhibitor has the structure

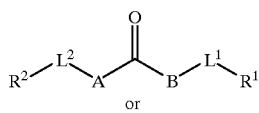

I or

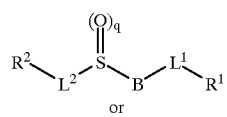

IA or

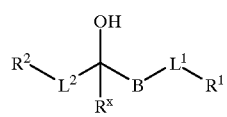

IB including pharmaceutically acceptable salts thereof, N-oxides thereof, wherein q is 0, 1 or 2;

A is (1) a bond;

(2) —O—; or

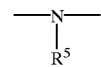

(3)

where $R^5$ is H or lower alkyl, or $R^5$ together with $R^2$ forms a carbocyclic or heterocyclic ring system containing 4 to 8 members in the ring;

B is a fluorenyl-type group of the structure

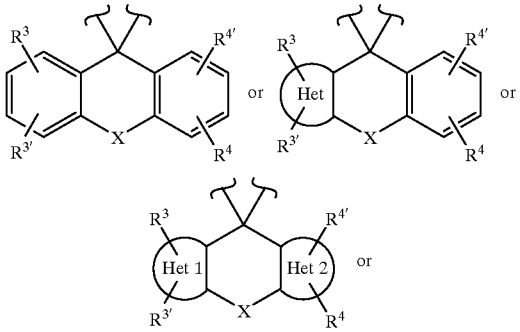

B is an indenyl-type group of the structure

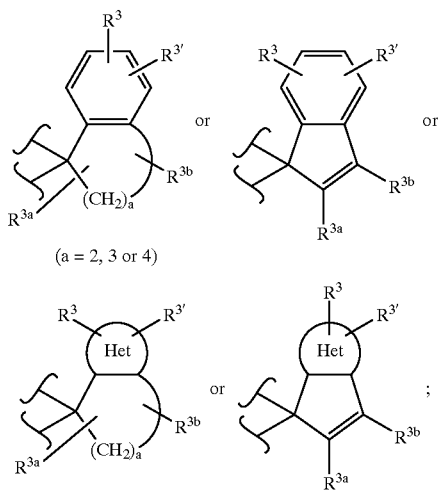

$R^x$ is H, alkyl or aryl;

$R^1$ is alkyl, alkenyl, alkynyl, alkoxyl, (alkyl or aryl)$_3$Si (there each alkyl or aryl group is independent), cycloalkyl, cycloalkenyl, substituted alkylamino, substituted arylalkylamino, aryl, arylalkyl, arylamino, aryloxy, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, —PO($R^{13}$) ($R^{14}$), (where $R^{13}$ and $R^{16}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); aminocarbonyl (where the amino may optionally be substituted with one or two aryl, alkyl or heteroaryl groups); cyano, 1,1-(alkoxyl or aryloxy)$_2$alkyl (where the two aryl or alkyl substituents can be independently defined, or linked to one another to form a ring connected to L¹ (or L² in the case of R²) at the 2-position); 1,3-dioxane or 1,3-dioxolane connected to L¹ (or L² in the case of R²) at the 4-position; the R¹ group may optionally be substituted with 1, 2, 3 or 4 substituents, which can be any of the R³ or R¹ groups or alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may optionally be substituted with alkyl, aryl or heteroaryl), heterocyclyl-carbonylamino (where the heterocycle is connected to the carbonyl group via a nitrogen or carbon atom), alkylsulfonylamino, arylsulfonylamino, heteroarylsulfonylamino,

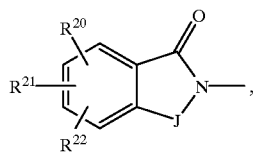

where J is: CHR²³, —C(=O)—, —CH(R²⁴)—CH(R²⁵)—, or —C(R²⁴)=C(R²⁵)—;

R²³, R²⁴ and R²⁵ are independently hydrogen, alkyl, alkenyl, alkynyl, aryl, arylalkyl, heteroaryl, heteroarylalkyl, cycloalkyl, or cycloalkylalkyl;

R²⁰, R²¹, R²² are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these substituents may either be directly attached to R¹, or attached via an alkylene at an open position;

R² is independently any of the groups set out for R¹, H, polyhaloalkyl, or cycloheteroalkyl, and may be optionally substituted with one to four of any of the groups defined for R³ or substituents defined for R¹;

L¹ is a linking group containing from 1 to 10 carbons in a linear chain including alkylene, alkenylene or alkynylene, which may contain, within the linking chain any of the following: one or two alkenes, one or two alkynes, an oxygen, an amino group, an oxo group, and may be substituted with one to five alkyl or halo groups;

L² may be the same or different from L¹ and may independently be any of the L¹ groups set out above or a singe bond;

R³, R³', R⁴ and R⁴' may be the same or different and are independently selected from H, halogen, CF₃, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar-, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

R³ᵃ and R³ᵇ are the same or different and are independently any of the R³ groups except hydroxy, nitro, amino or thio;

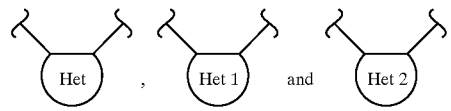

are the same or different and independently represent a 5 or 6 membered heteroaryl ring which contains 1, 2, 3 or 4 heteroatoms in the ring which are independently N, S or O; and including N-oxides;

X is a bond, or is one of the following groups:

(1)

(2)

(3)

(4)

(5)
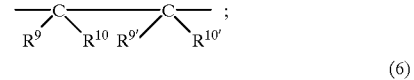

(6)
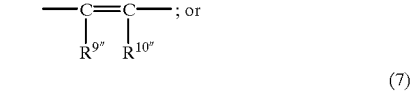

(7)

wherein
Y is O, N—R⁶ or S;
n' is 0, 1 or 2;
R⁶ is H, lower alkyl, aryl, —C(O)—R¹¹ or —C(O)—O—R¹¹,
R⁷ and R⁸ are the same or different and are independently H, alkyl, aryl, halogen, —O—R¹², or
R⁷ and R⁸ together can be oxygen to form a ketone;
R⁹, R¹⁰, R⁹' and R¹⁰' are the same or different and are independently H, lower alkyl, aryl or —O—R¹¹;
R⁹'' and R¹⁰'' are the same or different and are independently H, lower alkyl, aryl, halogen or —O—R¹¹;
R¹¹ is alky or aryl;
R¹² is H, alkyl or aryl.

21. The method as defined in claim 20 wherein the MTP inhibitor has the structure

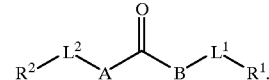

22. The method as defined in claim 21 wherein A is a bond.

23. The method as defined in claim 21 wherein A is —O—.

24. The method as defined in claim 21 wherein A is

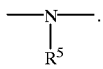

25. The method as defined in claim 21 wherein B is a fluorenyl-type group.

26. The method as defined in claim 21 having the formula

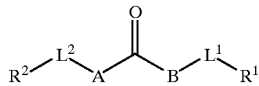

wherein B is

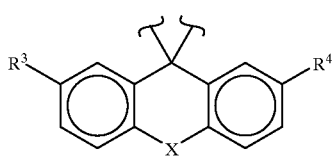

A is NH;

X is a bond, oxygen or sulfur;

$R^3$ and $R^4$ are the same or different and are H or F;

$R^1$ is aryl, phenyl, heteroaryl, imidazolyl, pyridyl, cyclohexyl, $PO(R^{13})(R^{14})$, heteroarylthio, benzthiazole-2-thio, imidazole-2-thio, alkyl, alkenyl, or 1,3dioxan-2-yl, wherein each of the above is optionally substituted;

$R^2$ is alkyl, polyfluoroalkyl, alkenyl, aryl, phenyl, heteroaryl, imidazolyl or pyridyl, wherein each of the above is optionally substituted;

$L^1$ is a chain containing 1 to 5 atoms in a linear chain;

$L^2$ is a bond or lower alkylene.

27. The method as defined in claim 1 wherein the MTP inhibitor has the structure

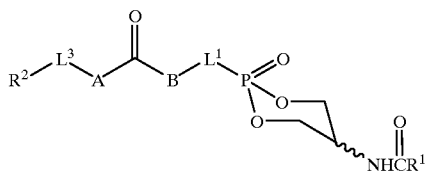

including pharmaceutically acceptable salts thereof, N-oxides thereof, wherein

A is (1) a bond;
(2) —O—; or

(3)

where $R^5$ is H or lower alkyl, or $R^5$ together with $R^2$ forms a carbocyclic or heterocyclic ring system containing 4 to 8 members in the ring;

B is a fluorenyl-type group of the structure

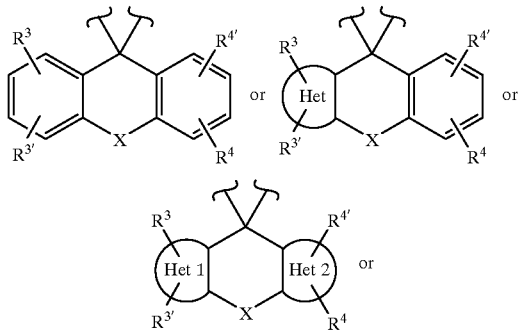

B is an indenyl-type group of the structure

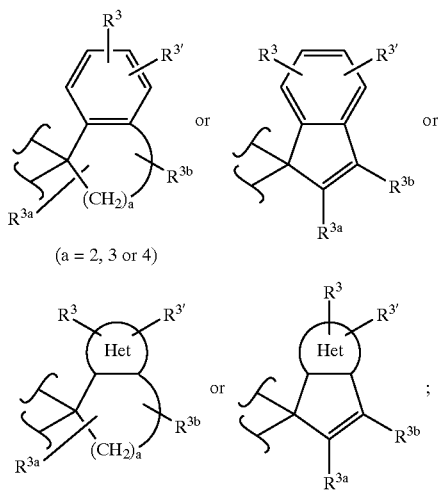

(a = 2, 3 or 4)

$R^x$ is H, alkyl or aryl;

$R^1$ is independently alkyl, alkenyl, alkynyl, aryl, alkoxy, aryloxy, arylalkoxy, heteroaryl, arylalkyl, heteroarylalkyl, cycloalkyl-, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, aryloycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonyl-amino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl;

$R^2$ is alkyl, alkynyl, alkynyl, alkoxyl, (alkyl or aryl)$_3$Si (where each alkyl or aryl group is independent), cycloalkyl, cycloalkenyl, substituted alkylamino, substituted arylalkylamino, aryl, arylalkyl, arylamino, aryloxy, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, —PO($R^{13}$) ($R^{14}$), (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); aminocarbonyl (where the amino may optionally be substituted with one or two aryl, alkyl or heteroaryl groups); cyano, 1,1-(alkoxyl or aryloxy)$_2$alkyl (where the two aryl or alkyl substituents can be independently defined, or linked to one another to form a ring connected to $L^1$ (or $L^2$ in the case of $R^2$) at the 2-position); 1,3-dioxane or 1,3-dioxolane connected to $L^1$ (or $L^2$ in the case of $R^2$) at the 4-position; the $R^2$ group may optionally be substituted with 1, 2, 3 or 4 substituents, which can be any of the $R^3$ or $R^1$ groups or alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may optionally be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino,

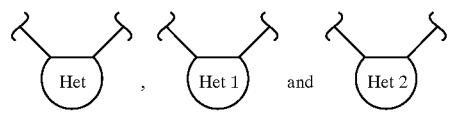

where J is: CHR$^{23}$, 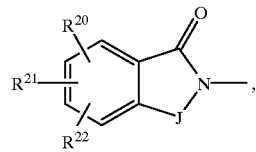

$R^{23}$, $R^{24}$ and $R^{25}$ are independently hydrogen, alkyl, alkenyl, alkynyl, aryl, arylalkyl, heteroaryl, heteroarylalkyl, cycloalkyl, or cycloalkylalkyl;

$R^{20}$, $R^{21}$, $R^{22}$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these substituents may either be directly attached to $R^1$, or attached via an alkylene at an open position;

$L^1$ is a linking group containing from 1 to 10 carbons in a linear chain including alkylene, alkenylene or alkynylene, which may contain, within the linking chain any of the following: one or two alkenes, one or two alkynes, an oxygen, an amino group, an oxo group, and may be substituted with one to five alkyl or halo groups;

$L^2$ may be the same or different from $L^1$ and may independently be any of the $L^1$ groups set out above or a singe bond;

$R^3$, $R^{3'}$, $R^4$ and $R^{4'}$ may be the same or different and are independently selected from H. halogen, CF$_3$, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar-, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

$R^{3a}$ and $R^{3b}$ are the same or different and are independently any of the $R^3$ groups except hydroxy, nitro, amino or thio;

are the same or different and independently represent a 5 or 6 membered heteroaryl ring which contains 1, 2, 3 or 4 heteroatoms in the ring which are independently N, S or O; and including N-oxides;

X is a bond, or is one of the following groups:

 (1)

 (2)

 (3)

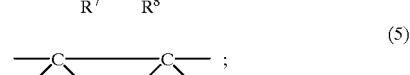 (4)

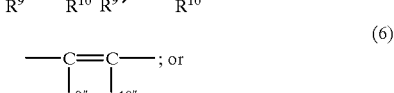 (5)

 (6)

(7)

wherein
Y is O, N—$R^6$ or S;
n' is 0, 1 or 2;
$R^6$ is H, lower alkyl, aryl, —C(O)—$R^{12}$, or —C(O)—O—$R^{11}$;
$R^7$ and $R^8$ are the same or different and are independently H, alkyl, aryl, halogen, —O—$R^{12}$, or
$R^7$ and $R^8$ together can be oxygen to form a ketone;
$R^9$, $R^{10}$, $R^{9'}$ and $R^{10'}$ are the same or different and are independently H, lower alkyl, aryl or —o—$R^{11}$;
$R^{9''}$ and $R^{10''}$ are the same or different and are independently H, lower alkyl, aryl, halogen or —O—$R^{11}$;
$R^{11}$ is alky or aryl;
$R^{12}$ is H, alkyl or aryl.

* * * * *